US012053218B2

(12) United States Patent
Sahin et al.

(10) Patent No.: US 12,053,218 B2
(45) Date of Patent: Aug. 6, 2024

(54) PRESHEARING METHOD FOR THE CONTROL OF THE RHEOLOGY AND THE INJECTABILITY OF AQUEOUS INORGANIC CEMENTS

(71) Applicants: Erdem Sahin, Izmir (TR); Dilhan M. Kalyon, Teaneck, NJ (US)

(72) Inventors: Erdem Sahin, Izmir (TR); Dilhan M. Kalyon, Teaneck, NJ (US)

( * ) Notice: Subject to any disclaimer, the term of this patent is extended or adjusted under 35 U.S.C. 154(b) by 356 days.

(21) Appl. No.: 17/384,859

(22) Filed: Jul. 26, 2021

(65) Prior Publication Data
US 2021/0353345 A1 Nov. 18, 2021

Related U.S. Application Data

(62) Division of application No. 15/966,185, filed on Apr. 30, 2018, now abandoned.

(51) Int. Cl.
A61B 17/88 (2006.01)
A61F 2/46 (2006.01)
(Continued)

(52) U.S. Cl.
CPC ...... *A61B 17/8802* (2013.01); *A61B 17/8805* (2013.01); *A61B 17/8822* (2013.01);
(Continued)

(58) Field of Classification Search
CPC ............ A61B 17/8802; A61B 17/8805; A61B 17/8822; A61B 17/8833; A61B 2017/8838
See application file for complete search history.

(56) References Cited

U.S. PATENT DOCUMENTS 1,934,116 A 11/1933 Canfield
3,151,995 A 10/1964 Nemeth
(Continued)

OTHER PUBLICATIONS

Şahin, E.; Kalyon, D.M. The rheological behavior of a fast-setting calcium phosphate bone cement and its dependence on deformation conditions, Journal of Mechanical Behavior of Biomedical Materials, May 2017, 72, 252-260, Elsevier.
(Continued)

*Primary Examiner* — Amy R Sipp

(57) ABSTRACT

The invention provides a system for the preshearing based control of the flow and deformation behavior, i.e., the setting kinetics, and the time dependent shear viscosity, elasticity of aqueous cementitious suspensions that can be used for bone repair and regeneration. The dynamic cement microstructure is tailored to the demands of the surgical tasks (faster/slower setting) or additive manufacturing tasks (lower/higher viscosity) by application of various preshearing conditions. Since the relationships between the preshearing and pressurization conditions and the setting kinetics and the time dependent changes in elasticity and viscosity are complex, a priori characterization of viscoelastic properties using the advanced rheological characterization technique of small-amplitude oscillatory rheometry is needed to enable such tailoring. The preshearing system is intended to give control on the injectability and setting time of any calcium phosphate cement formulation to the surgeon during an orthopedic surgery where a batch of bone cement is processed. Other possible utilizations of the system include controlling the setting kinetics, shear viscosity and facilitating the resultant flow stability of cementitious ceramic suspensions processed in direct ink writing assemblies for additive manufacturing of cement constructs, in injection systems for oil wells, restoration and fracking.

6 Claims, 10 Drawing Sheets

(51) Int. Cl.
- *B01F 27/722* (2022.01)
- *B01F 27/724* (2022.01)
- *B01F 35/21* (2022.01)
- *B01F 35/213* (2022.01)
- *B01F 35/22* (2022.01)
- *A61F 2/28* (2006.01)
- *B01F 25/451* (2022.01)
- *B01F 33/501* (2022.01)
- *B01F 35/33* (2022.01)
- *G01N 11/14* (2006.01)

(52) U.S. Cl.
CPC ........ *A61B 17/8833* (2013.01); *A61F 2/4601* (2013.01); *B01F 27/722* (2022.01); *B01F 27/724* (2022.01); *B01F 35/213* (2022.01); *B01F 35/2136* (2022.01); *B01F 35/2209* (2022.01); *A61B 2017/883* (2013.01); *A61B 2017/8838* (2013.01); *A61B 2017/8844* (2013.01); *A61F 2002/2817* (2013.01); *A61F 2002/4631* (2013.01); *B01F 25/451* (2022.01); *B01F 33/50112* (2022.01); *B01F 35/333* (2022.01); *G01N 11/142* (2013.01)

(56) References Cited

U.S. PATENT DOCUMENTS

| | | | |
|---|---|---|---|
| 4,202,413 A | 5/1980 | Messenger | |
| 5,071,040 A | 12/1991 | Laptewicz, Jr. | |
| 6,033,105 A | 3/2000 | Barker et al. | |
| 6,293,754 B1 | 9/2001 | Liang et al. | |
| 6,712,794 B2 | 3/2004 | Kust et al. | |
| 7,901,407 B2 | 3/2011 | Olson, Jr. et al. | |
| 8,403,888 B2 | 3/2013 | Gaudet | |
| 8,408,250 B2 | 4/2013 | McKay | |
| 8,409,211 B2 | 4/2013 | Baroud | |
| 8,834,481 B2 | 9/2014 | Murphy | |
| 8,870,888 B2 | 10/2014 | Steffen et al. | |
| 2004/0196735 A1 | 10/2004 | Barker et al. | |
| 2008/0065088 A1 | 3/2008 | Hughes et al. | |
| 2008/0154229 A1 | 6/2008 | Lambert | |
| 2009/0112365 A1 | 4/2009 | Orr et al. | |
| 2016/0278835 A1 | 9/2016 | Liang et al. | |
| 2016/0303278 A1* | 10/2016 | Stein | C08F 220/1818 |

OTHER PUBLICATIONS

Şahin, E. & Kalyon, D. M. Preshearing is an in situ setting modification method for inorganic bone cements. Medical Devices & Sensors, 3(6), 2020, e10105, Wiley.

Malik, M.; Kalyon, D.M.; Golba Jr, J.C. Simulation of co-rotating twin screw extrusion process subject to pressure-dependent wall slip at barrel and screw surfaces: 3D FEM Analysis for combinations of forward-and reverse-conveying screw elements, International Polymer Processing, Mar. 2014, 29-1: 51-62, Hanser.

Kalyon, D.M.; Malik, M. An integrated approach for numerical analysis of coupled flow and heat transfer in co- rotating twin screw extruders, International Polymer Processing, Jul. 2007, 22-3: 293-302, Hanser.

Yaras, P.; Kalyon, D.M.; Yilmazer, U. Flow instabilities in capillary flow of concentrated suspensions, Rheologica acta, Jan. 1994, 33-1, 48-59, Springer.

Yilmazer, U.; Gogos, C.G.; Kalyon, D.M. Mat formation and unstable flows of highly filled suspensions in capillaries and continuous processors, Polymer Composites, Aug. 1989, 242-248, 10-4, Wiley.

* cited by examiner

PRESHEARING METHOD FOR THE CONTROL OF THE RHEOLOGY AND THE INJECTABILITY OF AQUEOUS INORGANIC CEMENTS

BACKGROUND OF THE INVENTION

Technical Field

The present disclosure relates to inorganic cements used in bone repair and regeneration, and more particularly to methods and mechanisms for mixing, pressurization, and preshearing based in situ treatment for the control of the flowability, setting kinetics, and injectability/extrudability during manual or robotic delivery of such cementitious suspensions.

Prior Art

Cementitious materials are the materials of choice in design and manufacturing of structural, monolithic or injectable components due to their abundancy in nature, and by virtue of their flowability before setting. The latter is exploited most commonly in biomedical applications for bone repair and regeneration using calcium phosphate based cements (driven by the exceptional osteoconductivity of calcium phosphates) as injectable biomaterials (bone cement pastes) especially following cancerous bone removal and for minimally invasive surgeries. The minimally invasive clinical applications of bone cement pastes include spinal fusion, vertebroplasty, khyphoplasty, cranioplasty and periodontal surgery. Such inorganic bone cement pastes typically exhibit relatively low shear viscosity and elastic modulus and gain elasticity and shear viscosity with time. The rates of growths of the elasticity and viscosity of calcium phosphate based cements are higher than those of conventional cements as a result of the rapid dissolution and crystallization of various calcium phosphate phases in water. For this reason they are especially suitable for additive manufacturing of geometrically complex constructs where the deposited paste is made to gain elasticity for immediate shape retention. However additive manufacturing of relatively slow setting cementitious suspensions have been realized by pressurization through hoses of relatively large diameters (>10 mm) due to the propensity of such dynamically evolving suspensions for flow instabilities and related clogging issues during pressure-driven flows through narrow capillaries with diameters in the micronmeter scale.

During surgical applications the precise placement of the bone cement paste by the surgeon is very important. Various means are available for the placement of the cement paste Into the repair site. Generally a syringe with a hypodermic needle with a diameter around 1 mm can be used. During the injection of the cement paste a pressure drop of the ceramic paste is developed as the paste flows out of the syringe and the needle and as it is forced into the treatment site. This pressure drop represents the bottle neck to injection and is overcome by the surgeon applying a sufficient pressure on the ram of the syringe that holds the cement to overcome the pressure drop. The applicability and the injectability of the cement suspension are governed by the shear viscosity and the elasticity of the ceramic paste (functions of temperature, time, solid content and shear rate/stress). Once the ceramic suspension attains certain upper thresholds of viscosity and elasticity the injection of the cement paste to the treatment site via the pressure applied on the ram by the surgeon is no longer possible. The rapid increase of the shear viscosity of the cement paste (transition from flowable suspension to a gel and then to a rigid solid) is associated with the cement reaching its setting time. Thus, the setting time restricts the duration of time that the cement remains viable for injection during surgery. Currently in clinical practice, the setting time and flowability of the cementitious suspension are not adjustable parameters for a given formulation. The surgeon needs to select and use a suitable cement formulation (a commercial product which typically comes in a syringe or is mixed in the operating room) to obtain the targeted setting time and flowability.

Synthesis of ingredients for bone cements is intensively researched since there are unlimited combinations of possible constituents. The most popular methods for generation of new types of calcium phosphate based bone cements include the addition of chemical groups that have affinity to calcium ions such as citric acid or citrate salts to prolong the setting period, addition of salts to the cement setting liquid to increase the ionic strength and decrease the supersaturation of precursor ions, addition of phosphate containing salts such as sodium phosphate to increase the supersaturation, addition of acids to increase the solubility, and addition of chemicals like gentamycin that electrostatically stabilize calcium phosphate crystals by increasing their surface charge. The major problem that is faced is that every time there is a formulation change that involves the use of ingredients that are not approved by U.S. Food and Drug Administration, FDA, for in vivo usage, new and very costly FDA approvals may be necessary for implementation of these ingredients and formulations. Furthermore, the problem associated with the development of many choices for the surgeon is that the cement needs to be tailored via changes in composition to the specific application at hand. The surgeon currently has no recourse but to switch formulations depending on the requirements of the specific surgery since there are typically no adjustable parameters available during the injection of the bone cements to allow their tailoring for specific applications at the surgery site. Furthermore, multiple changes in flowability and elasticity may be necessary during the course of surgery to accommodate the complications that arise during surgery.

The mixing, conveying and delivery of aqueous inorganic cements are time consuming in practice when done manually and separately. The agitation mechanism in cement mixing trucks, introduced in U.S. Pat. No. 1,934,116 was a basic invention that significantly improved the efficiency of concrete casting. Bone cement mixing and delivery devices in particular have been invented recently, either as separate automated parts or as all-in-one facilities to improve the efficiency of preparation and delivery of the material during surgery operations under time constraint. Previous inventions that introduce novelty into the area are as follows. U.S. Patent #2008/0065088 A1 provides a mixing device for bone cements that is comprised of multiple chambers and pistons. U.S. Pat. No. 8,409,211 B2 introduces a bone cement delivery device with a tubular inner wall and a tubular outer wall, helical thread and vacuum and a pressure sensor. U.S. Patent #2008/0154229 A1 discloses a cement mixing and delivery device that uses a helical element and vibration to mix and deliver. These U.S. patents and applications lack method and control on the flow behavior, setting time and kinetics of the ceramic bone cements. Other bone cement delivery devices, such as a system for injecting a low viscosity fluid into a bone cement reservoir [U.S. Pat. No. 8,870,888 B2], a delivery device that uses a screw actuator to push the plunger [U.S. Pat. No. 6,712,794 B2], a delivery device that has an electronic actuator controller [U.S. Pat.

No. 8,403,888 B2], a device for transferring bone cement into a syringe for delivery [U.S. Pat. No. 8,408,250B2], a device for mixing polymeric bone cements effectively by utilization of helical blades [U.S. Pat. No. 6,033,105 A, U.S. Patent #2004/0196735 A1, U.S. Patent #2016/0278835 A1, U.S. Pat. No. 5,071,040] and a device which has a vibration element attached to the delivery needle [U.S. Pat. No. 8,834,481 B2, U.S. Pat. No. 7,901,407 B2] are available.

Overall, none of these methods and devices can control the rheology (flow and deformation behavior), the setting kinetics and the injectability/extrudability window of inorganic bone cements to accommodate the specific demands of a particular task that is 100 being undertaken. Mechanical modification of the setting processes of inorganic cements that include dissolution, nucleation and crystal growth was considered in the prior art for only their retardation until casting in constructions [U.S. Pat. No. 3,151,995]. On the other hand US Patent #2009/0112365 A1 discloses a method for determination and mechanical modification of the setting kinetics of polymerizable resin based cements used in orthopedic 105 applications. Various environmental factors including temperature, humidity, sound wave velocity, etc. within and around the polymeric resin have been correlated with this method to cement setting kinetics and the level of polymerization. Subsequent torsional or oscillatory mixing under non-specific stress conditions have been shown to facilitate the attainment of the level of maximum polymerization. In another disclosure on modification of rheology of fluids, U.S. Pat. No. 6,293,754 B1 explains direction of acoustic energy at frequencies between 1 kHz and 10 MHz to pressurized fluids for controlling viscosity by shear-thinning. The invention proposes a novel method of exploiting the shear-thinning mechanism and does not specifically apply to cementitious suspensions. In yet another method of agitation to alter the microstructure of cementitious suspensions, U.S. Pat. No. 4,202,413 discloses a method to improve the effectiveness of swelling clay particles that extend the inorganic cement suspension, by similar vigorous mixing. This method is only for the enhancement of the dispersion, swelling and extender function of inorganic, non-setting clay particles by the application of blending action of a rotating blade. Conversely, the preshearing method and mechanisms disclosed in the present invention utilize a distinctly different mechanism than shear-thinning and specifically apply to aqueous inorganic, non-polymerizable, cements such as calcium phosphate bone cements by employing torsional shear stresses at specific modes, rates and amplitudes that are determined upon accurate rheological characterization a priori in order to shorten or lengthen the setting times and to increase or decrease the resultant development of cement viscosity. The present invention serves to control the structural breakdown and recovery of inorganic cements also known as thixotropy. Clearly, there is a need for a method and mechanism to realize the in situ tailoring of the injectability, the shear viscosity, and elasticity of such ceramic paste materials, during surgery. In addition, extrusion through a sub-millimeter-diameter nozzle during robotic deposition of cementitious suspension necessitates such precise control of the evolving microstructure and pressurization conditions to achieve flow stability. The present disclosure provides a method and a mechanism that can address the aforementioned requirements for the effective utilization of inorganic cementitious suspensions for such applications.

BRIEF SUMMARY OF THE INVENTION

In view of the foregoing background, a method and a mechanism for the tailoring of the flow behavior (shear viscosity, elasticity), setting time and the workability/injectability of aqueous inorganic cements prior to or during the course of delivery by an orthopedic surgeon or a robotic additive manufacturing system are disclosed. The present disclosure specifically relates to the modification of flow properties of a ceramic cement suspension by preshearing (I.e., via subjecting the cementitious suspension to steady or oscillatory torsional deformations at critical values of the shear rate, shear strain and frequencies), pressurization (i.e., delivery of flowable cement through a capillary by a screw-driven mechanism) and a mechanism for both preshearing and pressurization. The present disclosure shows that the shear viscosity, elasticity and the setting kinetics of various relevant calcium phosphate cement formulations are dependent on such preshearing of the cement suspensions. Thus preshearing and simultaneous or subsequent pressurization by a handheld or robotically controlled device would allow specific tailoring of the flow properties and setting kinetics, and hence the control of the injectability/extrudability of the ceramic paste on one hand and the physical properties of the set cement on the other. The surgeon is given the freedom to choose the appropriate preshearing mode and preshearing parameters similar to considering different bone cement formulations that may be suitable for an application in terms of ease of injection, the setting time and ultimate mechanical properties. The invention also facilitates extrusion of cementitious suspensions for related applications including construction, structural restoration and additive manufacturing.

BRIEF DESCRIPTION OF THE DRAWINGS

For a more complete understanding of the present invention, reference is made to the following detailed description of an embodiment considered in conjunction with the accompanying drawings, in which.

Figure 7A:
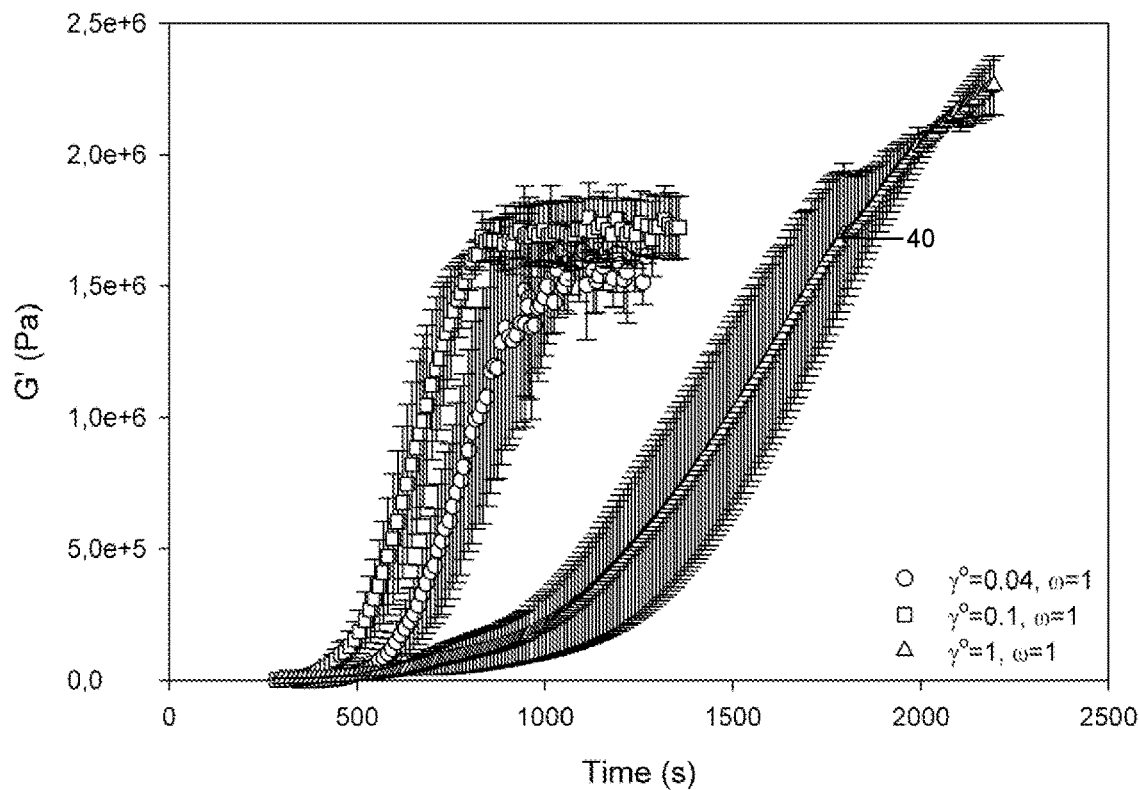
Figure 7B:
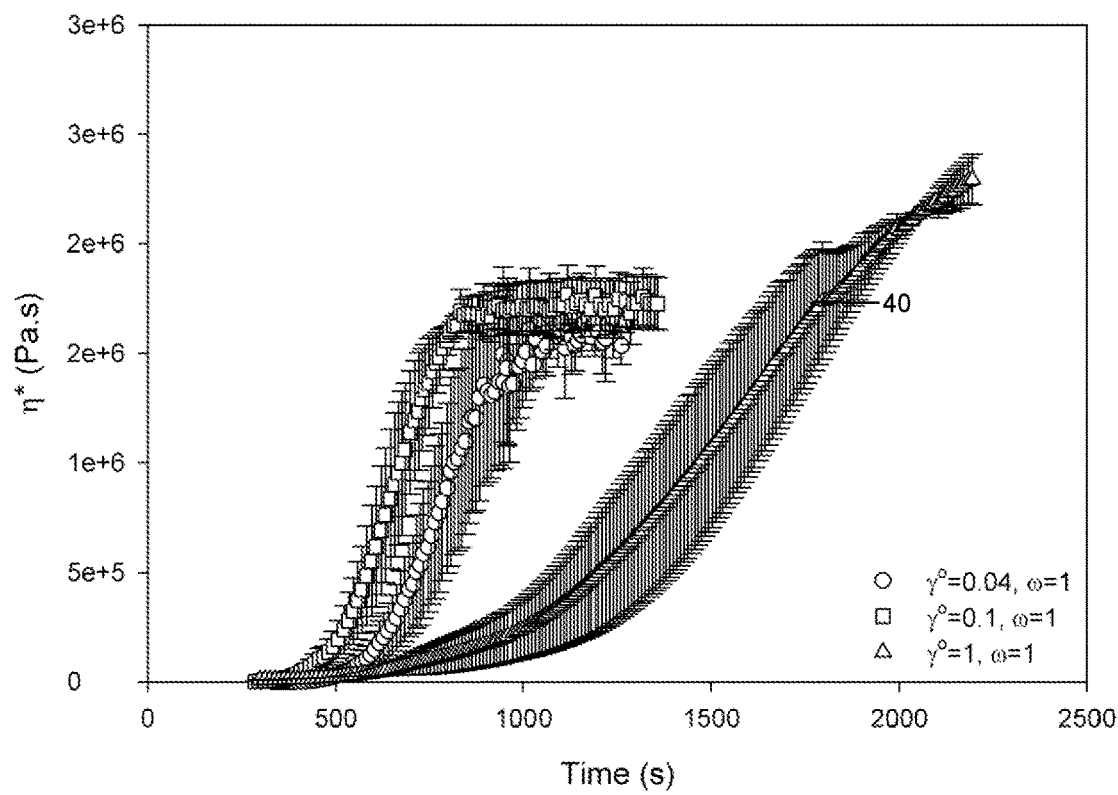
Figure 8A:
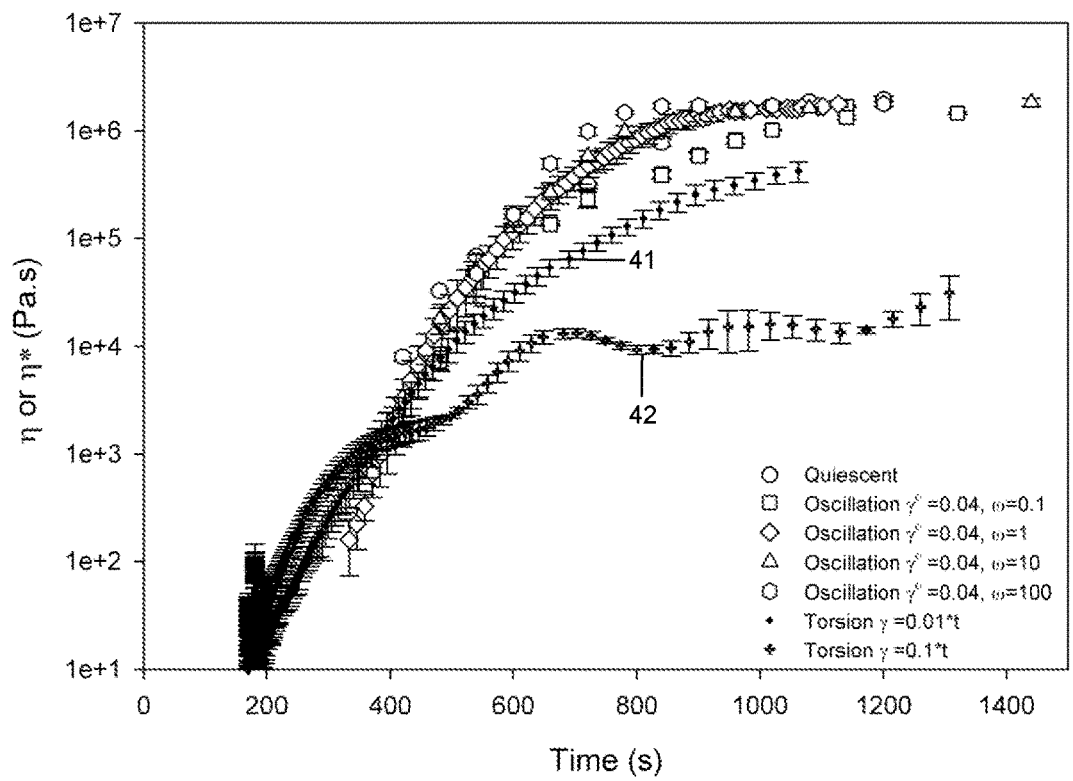
Figure 8B:
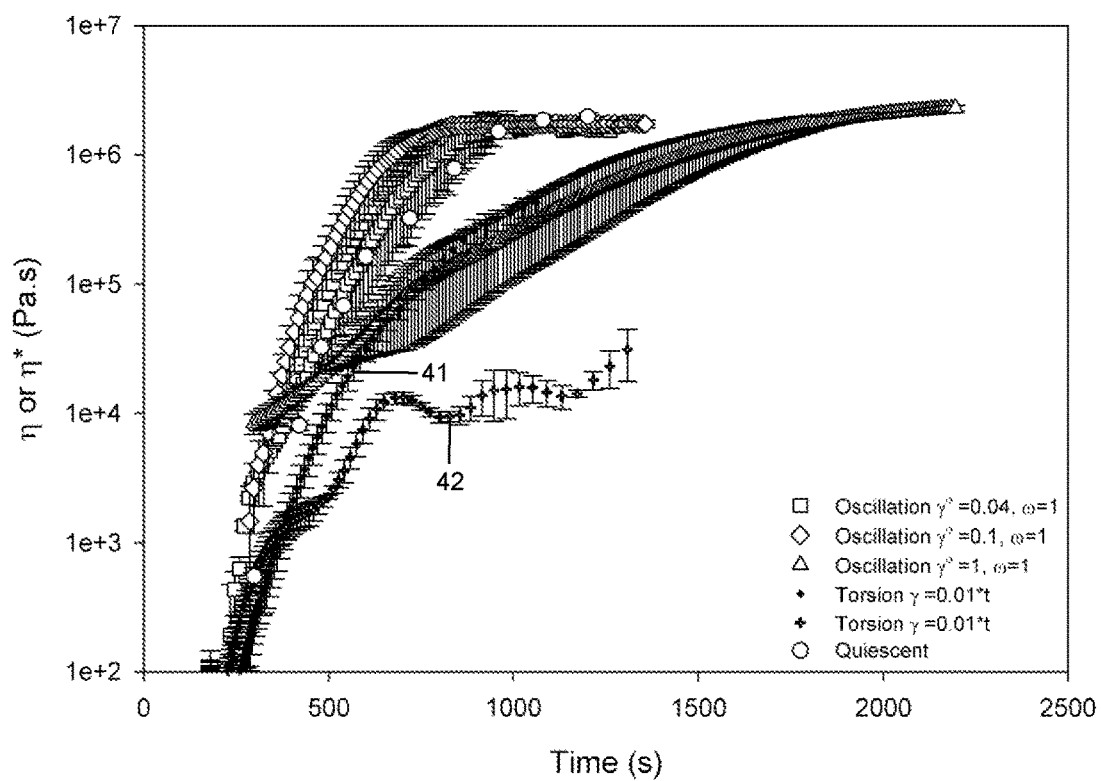
Figure 9A:
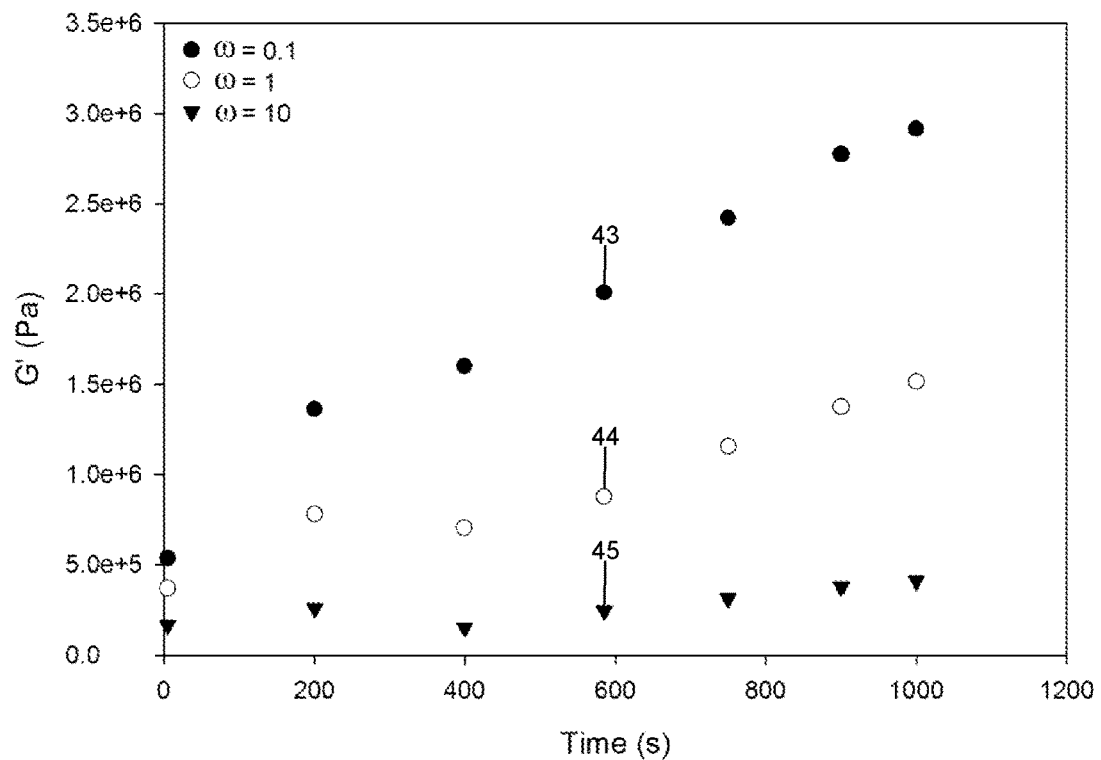
Figure 9B:
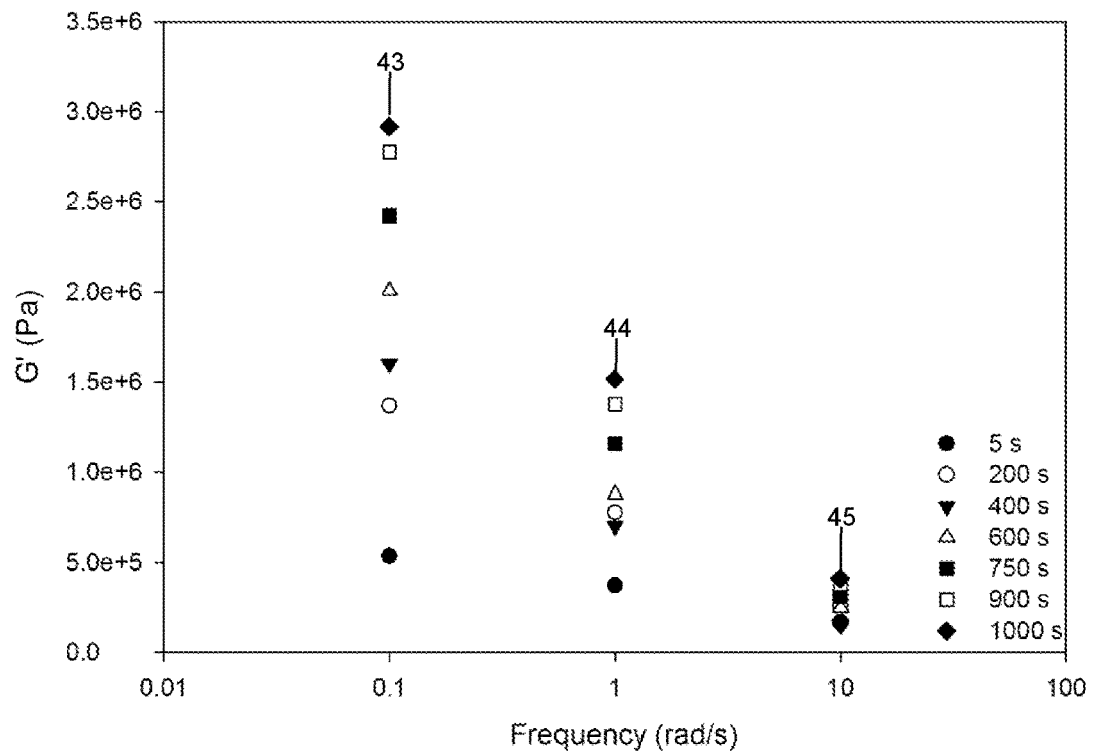
Figure 10:
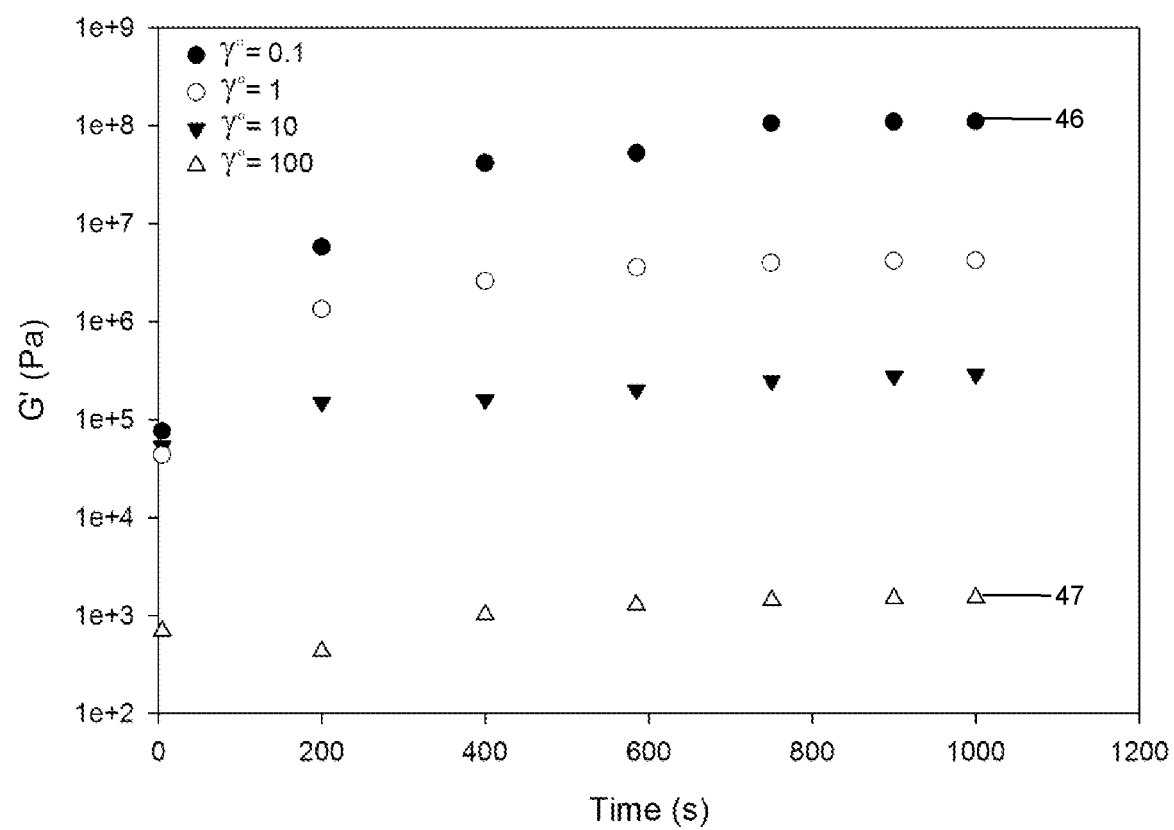
Figure 11A:
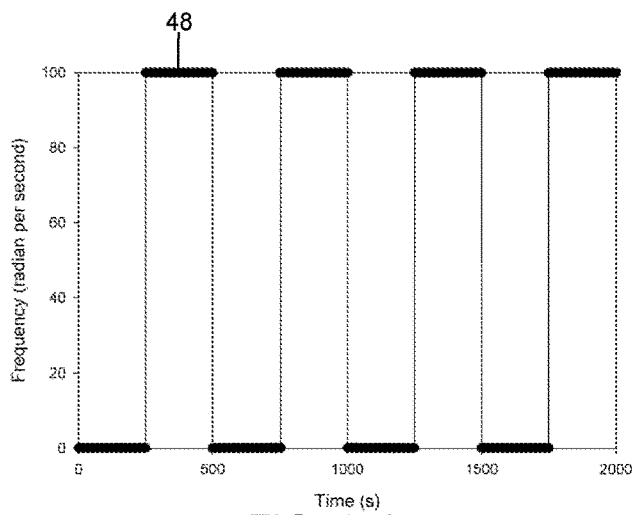
Figure 11B:
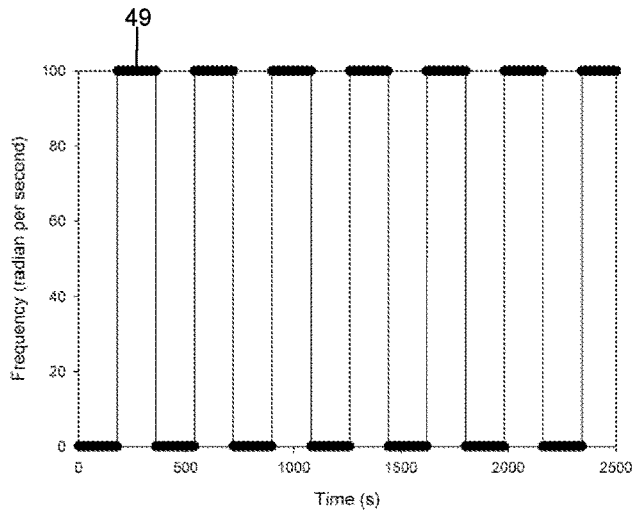
Figure 11C:
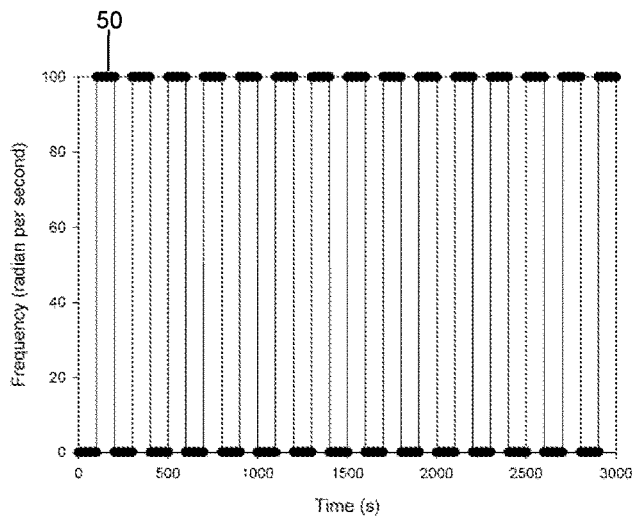
Figure 12:
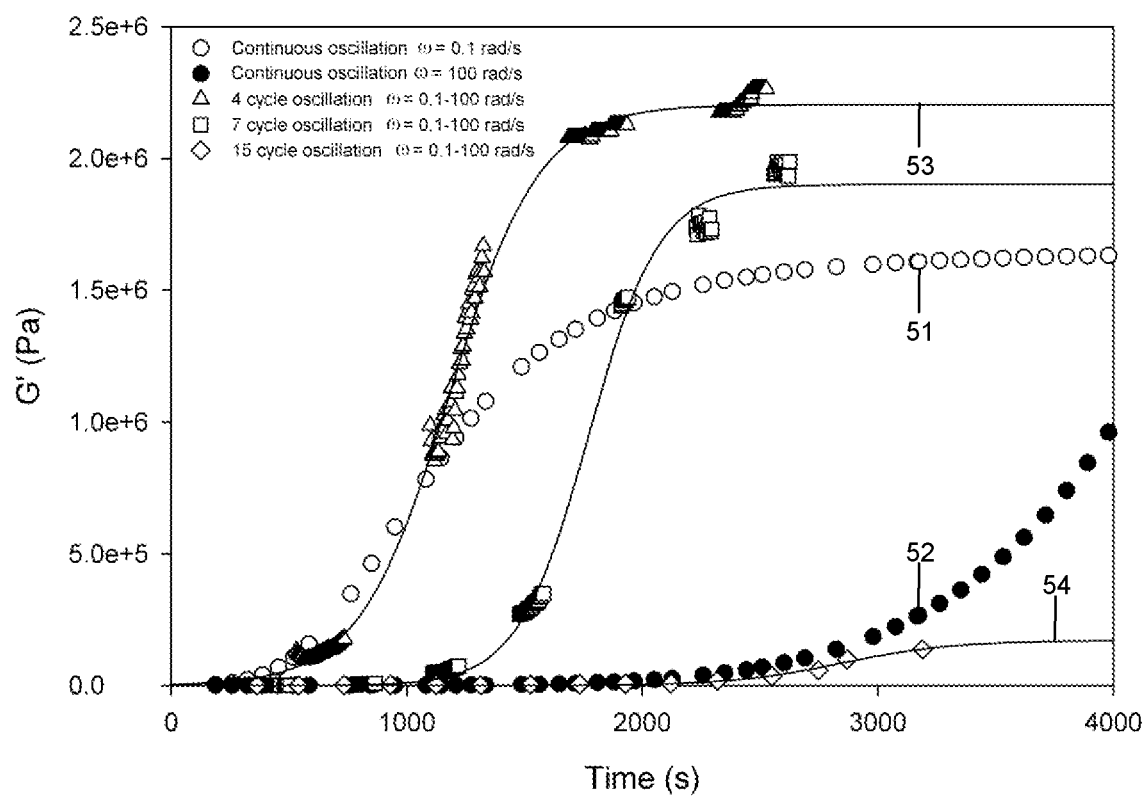

6A) and the magnitude of complex viscosity (FIG. 6B) for brushite cement samples that are not presheared (kept under quiescent conditions) and presheared at various frequencies at a strain amplitude of 0.04;

FIGS. 7A and 7B are a pair of charts showing the time-dependent development of the storage modulus (FIG. 7A) and the magnitude of complex viscosity (FIG. 7B) for cement samples that are presheared at various strain amplitudes at a frequency of 1 rps;

FIGS. 8A and 8B are a pair of charts showing the time-dependent development of the magnitude of complex viscosity when the preshearing involves steady torsional flow (constant shear rate) and oscillatory shearing at various frequencies (FIG. 8A) and strain amplitudes (FIG. 8B);

FIGS. 9A and 9B are a pair of charts showing the variation of the storage modulus, G', of bone cement as a function of time (FIG. 9A) and frequency (FIG. 9B) at a constant strain amplitude of 1;

FIG. 10 is a chart showing the time-dependent development of the storage modulus, G', of the bone cement as a function time at various strain amplitudes, $\gamma°$ and a constant frequency of 0.1 rps;

FIGS. 11A, 11B and 11C are a set of charts showing the cyclic changes in the frequency, i.e., from 0.1 rps to 100 rps, applied for 4, 7, and 15 cycles respectively; and FIG. 12 is a chart showing the time-dependent development of the storage modulus, G', of bone cement following cyclic changes in frequency during preshearing at various step sizes (strain amplitude is held constant at 1).

DETAILED DESCRIPTION OF THE EXEMPLARY EMBODIMENTS

The following disclosure is presented to provide an illustration of the general principles of the present invention and is not meant to limit, in any way, the inventive concepts contained herein. Moreover, the particular features described in this section can be used in combination with the other described features in each of the multitude of possible permutations and combinations contained herein.

All terms defined herein should be afforded their broadest possible interpretation, including any implied meanings as dictated by a reading of the specification as well as any words that a person having skill in the art and/or a dictionary, treatise, or similar authority would assign thereto.

Further, It should be noted that, as recited herein, the singular forms 'a,' "an," and "the" include the plural referents unless otherwise stated. Additionally, the terms "comprises" and "comprising" when used herein specify that certain features are present in that embodiment, however, this phrase should not be interpreted to preclude the presence or additional of additional steps, operations, features, components, and/or groups thereof.

The present disclosure generally relates to inorganic cement formulations, the rheological behavior and setting kinetics of which are very sensitive to preshearing. By definition, inorganic cements are single phase or a combination of ceramic powders that react with an aqueous setting solution. The mechanisms of the reactions may vary starting from hydration to dissolution, nucleation and crystallization. Initially flowable fluid mixture eventually gels, sets and hardens with time to a rigid mass with mechanical integrity. The invention is based on our recent observation that preshearing a cementitious calcium phosphate suspension in various shearing modes and under critical shearing conditions prior to injection can significantly increase or decrease the setting time, and thus can replace or complement the chemical setting retardants or enhancers that are utilized in the synthesis of clinically relevant calcium phosphate cements.

The present disclosure contemplates calcium phosphate and other types of inorganic cements that set at times close to or within the typical bone cement processing time of 10 to 45 minutes. Generally calcium phosphate cements with or without chemical retardants at the powder/liquid ratios between 1.0 and 4.5 and starting calcium phosphate particles with mean sizes that are generally less than 10 micrometers set within that period. Setting of water consuming cements like brushite forming calcium phosphate cements can generally be effectively retarded or delayed by preshearing whereas setting relatively slow setting cements like hydroxyapatite forming cements can generally be promoted by various mechanisms. Typical brushite forming cements set relatively rapidly in a few minutes and this period even shortens further when the water content decreases. For this reason setting retarder chemicals are necessary and become integral parts of most of the commercially available brushite forming calcium phosphate cements used in bone repair. The preshearing method and the mechanism offer the possibility to reduce/eliminate setting retarder or promoter chemicals from the cement formulation and their adverse effects on the biological and mechanical properties of the set biomaterial by increasing or decreasing the setting time mechanically.

The present disclosure discusses subjecting the cementitious ceramic formulations to time-dependent, strain amplitude-dependent or frequency-dependent shearing in a rheometer to determine the strain and strain rate conditions under which the setting of the ceramic paste is significantly altered. The rheometer is used to preshear the cement paste as well as to characterize the time dependent developments of its shear viscosity, elasticity, and injectability in a quiescent approach by removing the effect of strain history from measurements.

The present disclosure discloses a method comprising of subjecting the cementitious ceramic paste to predetermined preshearing conditions of shearing modes, shearing rates, and shearing strains in situ using a preshearing mechanism to control the time-dependency of the shear viscosity, and elasticity, hence the injectability of the bone cement using the data base generated by the use of the rheometer. The time it takes for cement paste to set can be increased or decreased by selecting the appropriate shearing mode (steady torsional flow versus oscillatory shear) or by selecting the appropriate values of the frequency or the strain amplitude in oscillatory shearing or shear rate in steady torsional flow.

The present disclosure also discusses the possible preshearing mechanisms for preshearing-based control of the rheology, setting times and injectability/extrudability of inorganic cementitious suspensions.

Preshearing Method for Control of Rheological Behavior and Setting Time (Injectability):

A preshearing method in accordance with an embodiment of the present invention has the following steps:
  (1) subjecting the cementitious ceramic formulation to steady or time-dependent preshearing in a small-amplitude oscillatory rheometer under systemically varied conditions of shear rate, shear strain amplitude and frequency;
  (2) characterization of the time-dependent development of shear viscosity, elasticity and setting kinetics following preshearing and determining the strain and strain rate conditions under which the setting of the ceramic paste is significantly altered; steps #1 and #2 being undertaken to determine a priori the relationship between preshearing conditions and provide guidance to the surgeon on the evolution of the time dependent shear viscosity and elasticity (and hence the injectability window) of the ceramic suspension on preshearing conditions;

(3) preshearing of the inorganic bone cement by the surgical staff or by a robotic operator using a preshearing device under the conditions that are necessary to achieve the desired injectability window of the bone cement on the basis of the timing requirements of the task on hand.

Characterization of the time-dependent development of shear viscosity, elasticity and setting kinetics following preshearing in the small amplitude oscillatory rheometer involves measurement of the mechanical response of the cement suspension to a predetermined torsional strain or stress state, as a function of time. Various strain modes, rates, amplitudes and frequencies are known to elicit different rheological behaviors in calcium phosphate cements. Conducting these measurements at relatively low strain amplitudes (below critical linear viscoelastic strain amplitude) and low frequencies in an oscillatory torsional rheometer ensures that the cement setting kinetics are probed at a condition closest to the quiescent equilibrium state when the setting characteristics of a specific cement formulation is clearly exhibited. Hence determination of the linear viscoelastic strain limit (LVSL) for a cement formulation is necessary prior to these measurements. The linear viscoelastic strain amplitude limit of a cement suspension increases with growing crystals as the cement sets and as temperature increases, and with viscous loss of mechanical wave energy as frequency decreases. Its dependence on frequency is weak so that a wide range of frequencies can be applied to cement suspensions without exceeding the LVSL.

The setting kinetics of a cement suspension is determined from the variation of the storage modulus (the primary measure of elasticity) with time using an oscillatory rheometer. Cement set at quiescent conditions represents the baseline reference in preshearing method with which various preshearing modes and conditions are related. Conventional testing in oscillatory rheometer is unable to precisely determine the setting kinetics of cements because of the effect of applied strain history on the setting kinetics. The only way to remove this effect is to partition the testing run into preshearing and measuring steps (or waiting and measuring steps for quiescent samples). This way the rheometer is used both to preshear the cement paste and to precisely characterize the time dependent developments of the shear viscosity, the elasticity and hence the injectability of the bone cement. During testing of quiescently setting cement this is accomplished by keeping the cement suspension at rest for various periods of time prior to the measurement step as demonstrated in the examples.

Figure 1B:
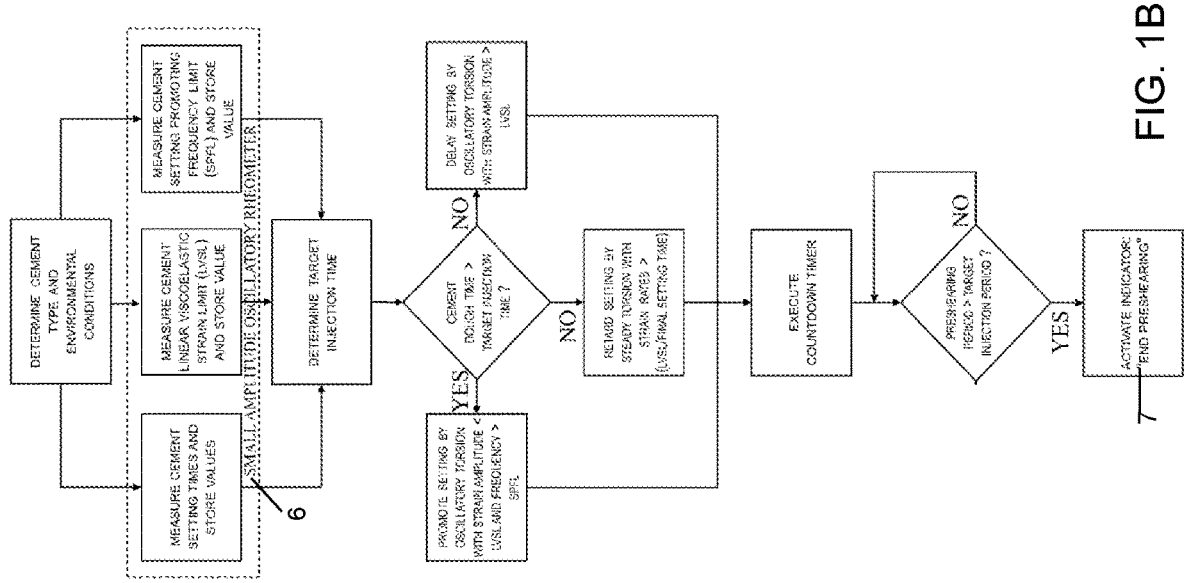
FIG. 1B is a flow chart showing standard procedural steps for utilization of the various modes of the preshearing method.
Figure 1A:
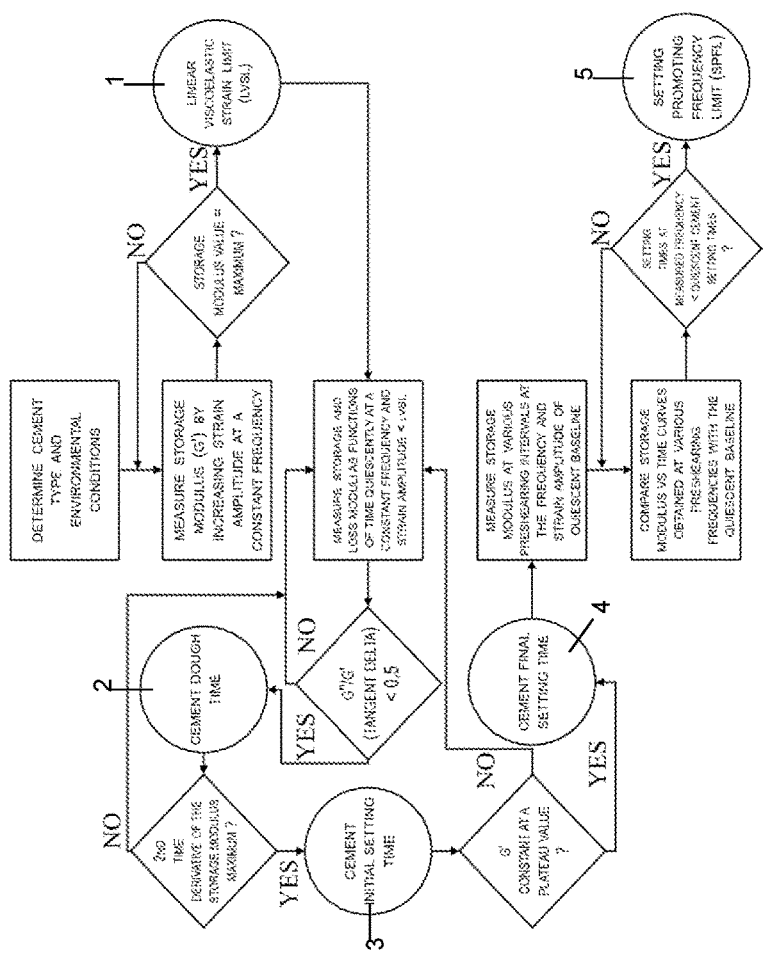
FIG. 1A is a flow chart showing the standard procedural steps of characterization of cements using a small amplitude oscillatory rheometer for predetermination of their key viscoelastic properties.

Testing the cement formulation at quiescent conditions and by preshearing in oscillatory rheometer at various frequencies enables the determination of five important properties for any cement system (the LVSL, the dough time, the initial setting time, the final setting time, and the setting promoting frequency limit (SPFL)) as shown in FIG. 1A and 1 n the example given later. The LVSL, 1, of a cement can be conveniently measured by subjecting the cement suspension sample to oscillatory torsion at a constant frequency and systematically increasing the strain amplitude from a low value (<1%) to macroscopically observable values, and determining the strain amplitude at which the dynamic properties start to decrease indicating the transition to nonlinear viscoelastic behavior. The dough time, 2 is the first of the setting times observed in rheological characterization during setting of a cement and it represents the end of injectability period when the suspension starts to thicken macroscopically. It is generally observed when the ratio of the loss modulus to the storage modulus (G"/G'=tan delta) decrease below 0.5. The initial setting time, 3 is the second kinetic data of importance as it indicates that cement has gained elasticity and further working it under pressure may damage the solid structure. It is observed when the second derivative of the storage modulus with respect to time reaches the maximum value. The final setting time, 4, the last of the kinetic data that marks the attainment of a rigid structure that can withstand pressure is observed when the storage modulus reaches a constant maximum value. SPFL, 5, is the analogue of LVSL to determine the critical frequency similar to the critical strain amplitude. It is the critical frequency that produces the same setting kinetics in comparison to the quiescently set cement at the constant strain amplitude used to measure quiescent cement properties. SPFL is determined iteratively and frequencies exceeding it promotes setting at strain amplitudes less than LVSL.

The alterations in the kinetic properties 2, 3, 4 resulting from the preshearing process are related to the baseline reference as promoting or delaying of the quiescent setting kinetics. These various preshearing effects are compiled and utilized as a guide for preshearing to tailor the setting kinetics by adjustment of the preshearing parameters. The preshearing method can be used to increase or to decrease the time it takes for the cement paste to set by selecting the appropriate shearing mode (steady torsional flow versus oscillatory shear) or by selecting the appropriate values of the frequency and the strain amplitude in oscillatory shearing or shear rate in steady torsional flow. The appropriate shearing mode and the parameters of shearing are obtained from rheological characterization 6 and applied according to the timing requirements of the task as described schematically in FIG. 1B. For example the setting of the cement formulation can be promoted to earlier times by increasing the frequency above a certain limit at a constant strain amplitude that does not exceed the LVSL, for a quick surgical task at hand, the limits being the rheological data outputs from the characterization step. Conversely its shear viscosity can be decreased by the delaying preshearing effect to facilitate pressurization for the targeted delivery rate of a robotic deposition device. For both manual and automatic preshearing operations, the extent of preshearing is critical for the effective modification of the setting kinetics. An indicator complements the preshearing process by providing the operator guidance on the extent of application to safeguard the intended microstructure of the presheared material. The "end preshearing", 7, indicates that preshearing period has exceeded the target delivery time. Manual or automatic delivery should end at that instant for optimum injectability/extrudability without excessive deformation.

We have recently reported that oscillatory torsional preshearing enhances the setting kinetics and decreases the setting times of calcium phosphate cements provided that the applied strain amplitude is below the LVSL and the frequency is higher than the SPFL. [E. Şahin, D. M. Kalyon, (2017) "The rheological behavior of a fast-setting calcium phosphate bone cement and its dependence on deformation conditions", Journal of the Mechanical Behavior of Biomedical Materials, Volume 72, 2017, Pages 252-260; E. Sahin, & D. M. Kalyon, (2020). Preshearing is an in situ setting modification method for Inorganic bone cements. Medical Devices & Sensors, 3(6), e10105.]. Accordingly, each unique cement system exhibits specific limits of these parameters that should be determined a priori according to the generally observed preshearing effects of oscillatory torsion given in Table 1. The strain amplitude is the primary parameter for the preshearing method whereas the frequency of the applied oscillatory torsional strain is a fine tuning parameter. Injection or extrusion time periods and viscosities of bone cements can be tailored by application of the findings from preshearing experiments.

TABLE 1

Effect of various combinations of oscillatory torsional strain amplitudes and frequencies on calcium phosphate cement setting kinetics

| Applied oscillation strain amplitude and frequency | Frequency higher than the SPFL | Frequency lower than the SPFL |
| --- | --- | --- |
| Strain amplitude lower than the LVSL | Positive effect (Lower setting time) | Negative effect (Higher setting time) |
| Strain amplitude higher than the LVSL | Negative effect (Higher setting time) | Negative effect (Higher setting time) |

In theory, the mechanical energy applied to a cementitious suspension by oscillatory torsion is proportional to the strain amplitude. The viscous drag force on the particle is critical for the integrity of the inter-particle network that forms during setting of a cementitious suspension. At high applied energy levels particles and inter-particle crystal bonds disrupt and cement setting is retarded. This critical energy level for any suspension is manifested by the deviation from linear viscoelastic behavior and accurately monitored as a function of time by small amplitude oscillatory rheometry.

A drag flow mechanism such as a rotating plate or a rotating screw can generate and apply targeted strain rates and strains as a function of time for preshearing-based control of the rheology and setting time of cementitious ceramic suspensions. The characterization steps provide the surgeon or robotic operator with a wealth of information as to how to control the injectability and workability of the bone cement via changes in the operating parameters of the preshearing mechanism which may also be capable of on-site mixing of the Ingredients of the ceramic paste formulation and on-site pressurization and the delivery of the ceramic paste to the treatment site or the translating printing stage.

Figure 2A:
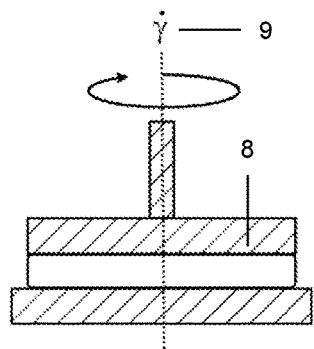
FIG. 2A is a schematic diagram of a parallel plate rotational rheometer and steady torsional mode of preshearing.
Figure 2A:
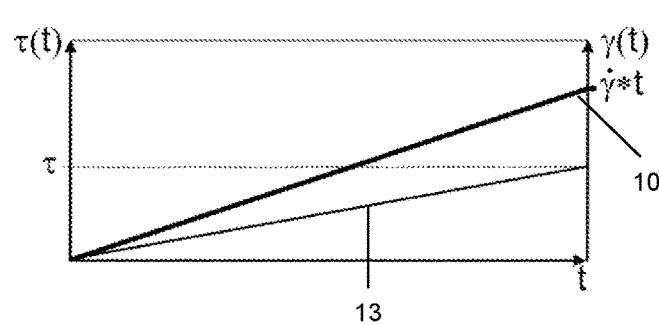
Figure 2B:
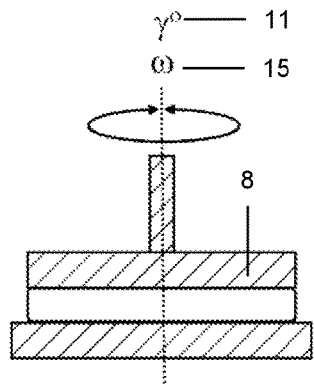
FIG. 2B is a schematic diagram of a parallel plate rotational rheometer and oscillatory torsional mode of preshearing.
Figure 2B:
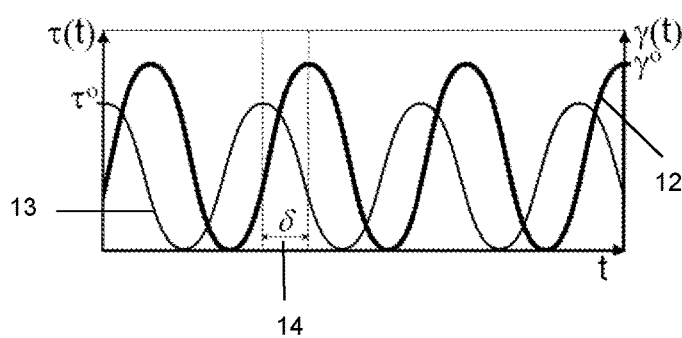

FIGS. 2A and 2B give the schematics of the steady and oscillatory torsional modes of application of drag shear forces to cementitious suspensions between circular plates 8, i.e. preshearing by torsion of the suspension. The strain rate ($\dot{\gamma}$), 9, applied during steady torsional preshearing (strain monotonously increasing with time t, i.e., the integral of the strain rate that is imposed, $\gamma=(\dot{\gamma})*t$, 10), and the strain amplitude $\gamma°$, 11, applied to the cement suspension during oscillatory torsional preshearing (strain cyclically applied in the form of a sinus wave as $\gamma=\gamma° \sin \omega t$, 12) mainly determine the extent of the retardation of cement setting. Shear stresses $\tau$, 13 develop in the cement in response to the applied strains $\gamma$, 10 and 12, according to the Hooke's law and depending on the shear modulus G, if the deformation occurs linear viscoelastically ($\tau=G*(\dot{\gamma})*t$ or $\tau=G*\gamma° \sin(\omega t+\delta)$). There exists a phase difference $\delta$, 14 between the applied oscillatory strain and the resultant stress due to the viscoelastic character of the material. Hence the oscillatory torsion mode of a rotational rheometer (FIG. 2B) is an effective tool to discern information about the viscous and elastic character of a fluid according to the phase difference $\delta$, by virtue of the cyclic nature of the deformation and the adjustable frequency $\omega$, 15, i.e., the time frame of a cycle of deformation.

The crystal network forming during setting is prone to structural damage when the applied oscillatory or torsional strains exceed the linear viscoelastic strain limit as crystals cannot attenuate the applied deformation energy elastically and break. This limit increases with the cement setting extent since bigger, well developed crystals are stronger. Hence the effectiveness of applied strain amplitudes or shear strain rates depend on the setting kinetics of a particular cement formulation which can be determined by the empirical methods mentioned above. Furthermore, different preshearing modes have the capability to delay or retard the setting of calcium phosphate cements. Oscillatory torsional strains exceeding the linear viscoelastic strain limit cause a temporary reduction in cement setting extent as setting recovery occurs subsequently. Alternatively steady torsional strains applied to a calcium phosphate cement suspension cause continuous damage to the forming crystal network due to the monotonous increase in strain at a rate higher than the crystal growth rate.

Still referring to FIG. 2B, frequency $\omega$, 15, of the applied oscillation energy determines the rate of energy transfer and affects time dependent processes in cement setting including dissolution, crystallization, and ion transportation. Higher frequencies cause an improvement in diffusion of calcium and phosphate ions similar to the effect of increasing temperature of the cement suspension. The effectiveness of this mechanism depends on the variation of the LVSL with frequency as well as the intrinsic chemistry of the cement suspension such as the concentration of ions and the extents of the dissolution, nucleation and crystallization of species in a specific cement formulation at a particular setting time. As these properties are very hard to model mathematically for any cement suspension system containing multiple phases and chemical species, an empirical correlation between the chemistry of the cement formulation and the effect of preshearing parameters needs to be sought using a rheometer. Hence preshearing method is basically an implementation of time-dependent microstructural control on cementitious suspensions based on the utilization of advanced rheological techniques as a means to accurately map the dynamic cement setting kinetics.

Figure 3A:
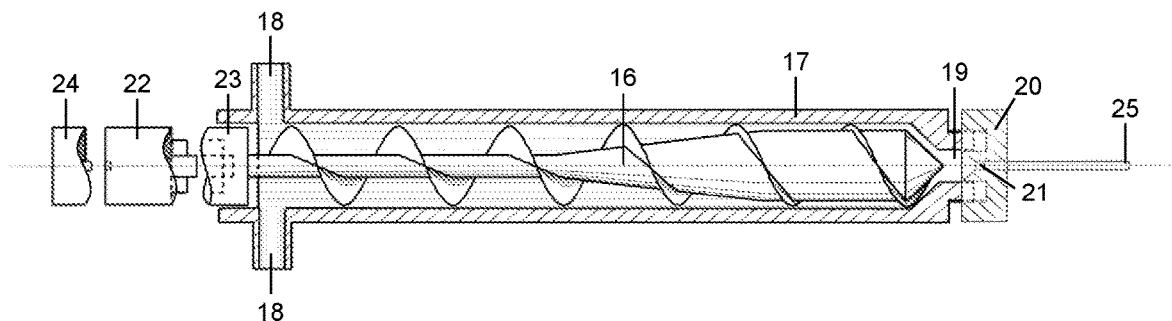
FIG. 3A is a schematic diagram of a preshearing mechanism constructed in accordance with an embodiment of the present invention, the preshearing device being configured for batch processing and injection to a treatment site.
Figure 3B:
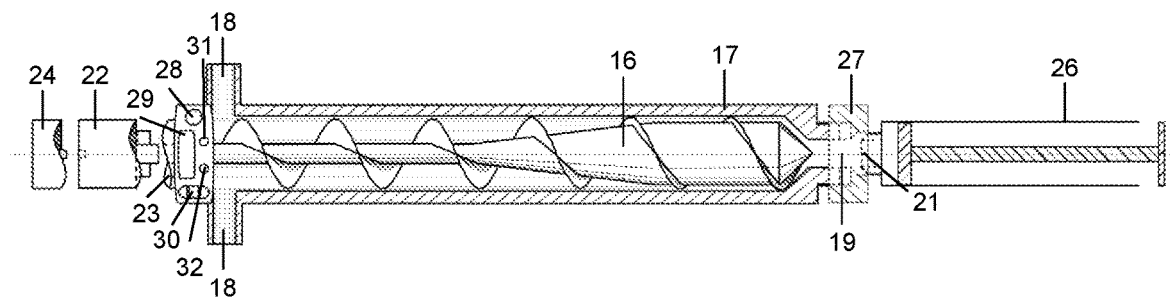
FIG. 3B is a schematic diagram of the preshearing device in FIG. 3A configured to pump bone cement into a syringe.

FIGS. 3A and 3B show schematics of a extruding preshearing mechanism in accordance with another embodiments of the present invention. Accordingly, the preshearing based control of the viscosity, elasticity and the setting time of injectable aqueous inorganic cement suspensions can be realized using a rotating and oscillating screw mechanism that is placed inside a barrel. Such a mechanism involving a cyclic extrusion system can be used to first mix the ingredients of the cement formulation if such mixing is necessary, and following mixing, for the preshearing of the cement paste at frequencies, strains, or strain rates that are identified a priori to be effective in delaying/promoting the setting of the cement and the decreasing/increasing of the elasticity and the shear viscosity of the bone cement. This preshearing mechanism is not a conventional single screw or twin screw extruder. The screw(s) (only one screw if the device is based on single screw extrusion, schematic of which is seen in FIG. 3A, 16, or two screws if the device is based on a twin screw extruder) of the preshearing mechanism do not rotate in the same direction but can oscillate between clockwise ("CW"), and counterclockwise ("CCW") directions at the desired frequencies to generate the identified oscillatory strains and steady strain rates as a function of time. There are comprehensive mathematical models and simulation packages which would allow the translation of the desired frequencies and strains obtained via the use of the rheometer to the operating parameters of the extruding preshearing mechanism [M. Malik, D. M. Kalyon, and J. C. Golba Jr., "Simulation of co-rotating twin screw extrusion process subject to pressure-dependent wall slip at barrel and screw surfaces: 3D FEM Analysis for combinations of forward- and reverse-conveying screw elements", International Polymer Processing, 29, 1, 51-62 (2014); D. Kalyon and M. Malik, "An integrated approach for numerical analysis of coupled flow and heat transfer in co-rotating twin screw extruders", International Polymer Processing, 22, 293-302 (2007)] and these capabilities can be used for each formulation to determine what the operating parameters of the preshearing device should be (screw speeds, CW or CCW rotation based oscillations) to generate the strain histories that are suggested by the rheometry tests.

Still referring to FIGS. 3A and 3B, the extruding preshearing mechanism comprising screw(s) 16 and barrel(s) 17, has inlet ports 18 to allow the feeding of various ingredients of the bone cement formulation if mixing is desired and the facility to rotate the screw/s in sequential or cyclic manner. Furthermore, the preshearing device has an exit gate 19 that is attached preferentially by a screw mechanism to a die 20 that can fully or partially seal the exit off by a manually or automatically closing a plug 21. If mixing of the ingredients of the formulation is desired, the ingredients of the formulation are fed into the extrusion hardware through ports 18 with the device fixed on a table top and with attachments to solid and liquid feeders. The screw(s) is/are steadily rotated by an electronically controlled gear box 22 that is connected to the screw shaft 23 and powered by the power pack 24 in the forwarding direction to allow the introduction of the ingredients into the mixing volume of the preshearing device that is operated in the batch configuration. Inlet ports 18 are closed manually or automatically upon completion of the feeding of the ingredients. The screw(s) is/are continued to be rotated by the gear box 22 for mixing and conveying of the cement. The exit gate 19 is initially sealed by closing the plug 21 so that the resulting circulation and back-mixing of the ingredients in the mixer gives rise to a well-mixed bone cement paste.

After the completion of the interspersing of the ingredients (mixing) additional rotation and oscillation of the screw(s) is/are carried out. This stage is defined as the "preshearing prior to delivery/injection" stage. During preshearing the shear rate and the shear strain history are tailored to affect the setting kinetics and the time-dependent development of the viscosity and the elasticity of the ceramic paste. For example, the increase of the rotational speed of the screw increases the shear rates that the cement paste is exposed to. Thus, the duration of the preshearing and the shear rate and strain history that are applied during preshearing become parameters that the operating room personnel can adjust according to the requirements of the specific surgery. This can conveniently be done by manually entering the parameters to the electrically controlled gear box through a control unit shown in FIG. 3B. The device can be powered by a single button 28 on the control unit. The modes and parameters of operation are read on the digital screen 29, and can be controlled by using a set of adjustment buttons 30. The control unit also contains an indicator 31 that assists the operator by visually indicating when preshearing can safely be ended 7 which are determined according to the algorithm explained in FIG. 1B. A visual indicator 32 of the power pack charging level serves to warn the operator when the device has to be charged.

Applied shear rate, time and strain history would alter the setting time and shear viscosity and the elasticity (i.e., the injectability, workability and the setting time) of the cementitious ceramic paste. Therefore, with a single formulation a wide range of setting times, shear viscosity and elasticity behavior (i.e., a range of injectabilities and working times) become possible. Another novelty of the mechanism is its capability to generate sequential cyclic oscillatory shearing during which the frequency of the deformation can be altered from one value to another in a cyclic manner. As shown in the examples, the most effective mode of preshearing involves the application of multiple frequencies during oscillatory shearing.

In the final step, the gate 19 of the extruding preshearing device that connects the barrel 17 and the die 21 acting as the nozzle is opened. Manual timing is the default in clinical practice due to the manual nature of the operations and automatic timing is the default for robotic deposition. In the embodiment shown in FIG. 3A, the device is equipped with a hypodermic needle 25 to perform direct injection of the presheared cement. In this case, the unit is detached from its feeder connections that are not shown in the figure, with sealing of the inlet ports and used as a pumping device. Cementitious suspension of appropriate viscosity and elasticity is discharged during the final step via the steady rotation of the screw(s) acting as a pressurizing pump at a predetermined rate that is suitable delivery rate. Discharged bone cement may also be transferred to a syringe 26 (see FIG. 3B) using different adapters as the die 27.

The critical preshearing parameters that should be exceeded or avoided for the promotion, delaying or retardation of setting of various clinically relevant calcium phosphate cement formulations were determined as well as the setting times at various preshearing conditions and discussed in the following examples where a rotating parallel plate rheometer with the capability of applying small oscillation amplitudes was utilized as both the characterization and the preshearing device.

Example 1

The formulations and the preshearing method have been tested using a small amplitude oscillatory rheometer, i.e., a parallel plate based shearing device with one plate (disk) stationary and the second either rotating in one direction continuously (CW or CCW) or oscillating between CW and CCW directions. The shearing device has the ability to impose a constant or cyclic shear rate and to measure the torque and the normal force as a function of time, temperature and rate of shear. The rheometer can thus characterize the elasticity and the shear viscosity of the cement paste as a function of the previous shearing history. The diameter of the two disks can be varied between 8 to 50 mm. The calcium phosphate cement formulations of this invention are placed in between the two plates at a typical gap of separation of 0.5 to 4 mm. In the steady torsional mode the shearing device can typically generate shear rates which are in the range 0.01 to 100 1/s (the shear rate is defined as the linear velocity of the disk over the gap between the two discs). At the oscillating mode the typical sinusoidal shear strain and shear stress waves are obtained. The typical frequency range is 0.01 to 1000 rad/s (rps).

Brushite forming calcium phosphate cement formulation was mixed with powder/liquid ratio of 1.0, 1 wt % brushite seed and citric acid concentration of 0.5 M using a sonicator for 60 seconds according to the stoichiometry of the following setting reaction and transferred to the shearing device.

$\beta\text{-}Ca_3(PO_4)_2 + Ca(H_2PO_4)_2 \cdot H_2O + 7H_2O \rightarrow 4CaHPO_4 \cdot 2H_2O$ The characteristic starting particle sizes were in the 2 μm range. The temperature of the sample holder chamber was set to 25° C. The preshearing device was operated at two modes: steady flow (steady torsional) and oscillatory flow (oscillatory torsional) to preshear the bone cement at different shearing modes and with different frequency and amplitude for oscillatory shearing and at different shear rates for steady torsional flow based shearing and for different durations. Furthermore, the dynamic moduli (storage modulus, G', which represents the amount of energy stored as elastic energy during one cycle of deformation "the elasticity" and loss modulus, G", which represents the energy dissipated as heat during one cycle of deformation, the magnitude of complex viscosity η* (the value of which approaches the shear viscosity as the shear rate and frequency approach zero), tangent (δ)=G"/G' and normal stress were measured as functions of time by oscillatory torsional flow at various frequencies of 0.1 rad/s, 1 rad/s, 10 rad/s, 100 rad/s and at various strain amplitudes.

Figure 4:
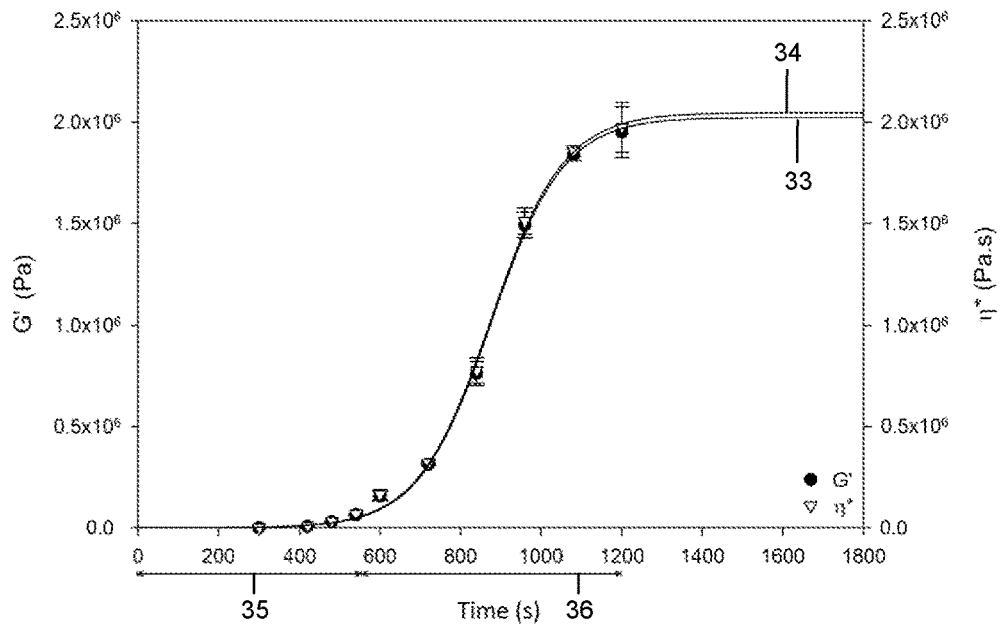
FIG. 4 is a chart showing the time-dependent setting behavior of a ceramic sample held under quiescent conditions, as represented by its elastic storage modulus, G', and its magnitude of complex viscosity, $\eta^*$ wherein each point refers to a specific elapsed time under quiescent conditions (without shearing) following mixing.

The development of the storage modulus, G' and the magnitude of complex viscosity, η* of the bone cement sample that is kept under quiescent conditions with time are shown in FIG. 4. The elasticity (as represented by the storage modulus, G' 33) and the viscosity (as represented by the magnitude of complex viscosity 34) increase in parallel as a function of time during which the sample is held under quiescent conditions. Each point refers to a specific elapsed time under quiescent conditions (without shearing) following mixing and it belongs to the average of measurements from different cement samples. Starting each measurement with a freshly prepared cement sample is necessary to eliminate the strain history. The curve fits of the data points represent the setting curves 33 and 34. The cement is typically injectable until the initial setting time (injection period 35) when the storage modulus (setting rate) starts to abruptly increase. It is measured as the time when the second derivative of storage modulus reached maximum value and the final setting time is conveniently determined from the plateau region of the storage modulus vs time curve. Any manipulation of the cement needs to be avoided during this setting period 36 that spans the majority of the duration after mixing of the cement with water.

These data obtained for quiescent conditions indicate that this specific formulation would have relatively low elasticity and shear viscosity for about 600 s following mixing. The bone cement starts to harden at a relatively high rate after 600 s and becomes completely solid-like in 1200 s, at which time the bone cement would not flow at all. Thus, upon mixing this specific formulation needs to be delivered into the treatment site by the surgeon within 10-20 minutes, with the maximum time cut-off depending on what the surgeon needs in terms of viscosity and elasticity of the bone cement. It should be noted that this is a water based formulation and would require some thickening prior to injection otherwise there will be significant demixing (segregation) effects during injection through a needle (see references on segregation of suspensions with relatively low viscosity binders [Yaras et al., "Flow Instabilities in Capillary Flow of Concentrated Suspensions," Rheologica Acta, 33, 48-59 (1994); Yilmazer et al., "Mat Formation and Unstable Flows of Highly Filled Suspensions in Capillaries and Continuous Processors," Polymer Composites, 10 (4), 242-248(1989)]

Figure 5:
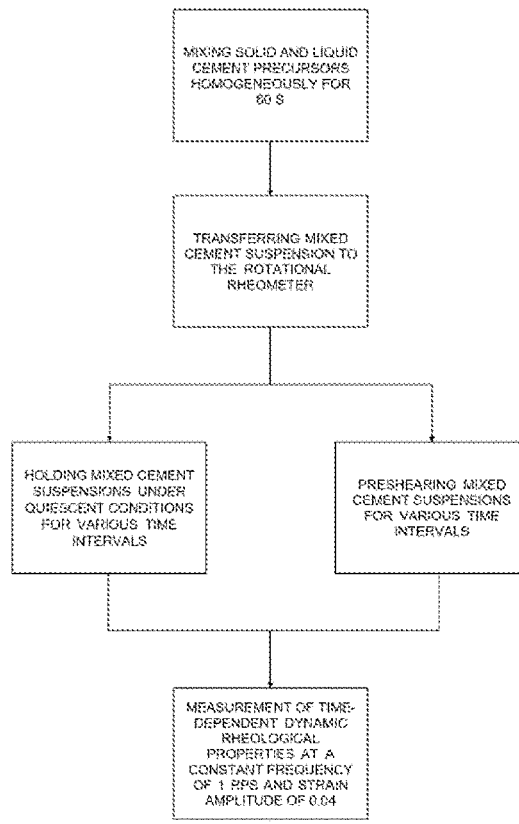
FIG. 5 is a flow chart showing the partitioning between the data measurement and application of the effects of preshearing to conduct measurement of the time-dependent rheological behavior and setting kinetics without creating strain history.

The schematics of how the preshearing effect is documented are shown in FIG. 5. In one set of experiments the bone cement was held under quiescent conditions (no preshearing) for various durations of time and then its dynamic properties, i.e., storage modulus, G', which represents "the elasticity" and loss modulus, G", which represents the energy dissipated as heat during one cycle of deformation, and the magnitude of complex viscosity η* were characterized as a function of time at a constant frequency of 1 rps and at a constant strain amplitude of 0.04. In a second series of experiments the bone cement was presheared at various strain amplitudes, γ° and frequencies, ω for various durations and then subjected to the same oscillatory shear parameters of frequency of 1 rps and strain amplitude of 0.04 and time dependent development of the elasticity and viscosity were documented. Thus, following preshearing or quiescent conditions for the same durations of time, the time dependent elasticity and viscosity behavior of the bone cement was documented by collecting the dynamic properties as a function of time at 1 rps and strain amplitude of 0.04.

Figure 6A:
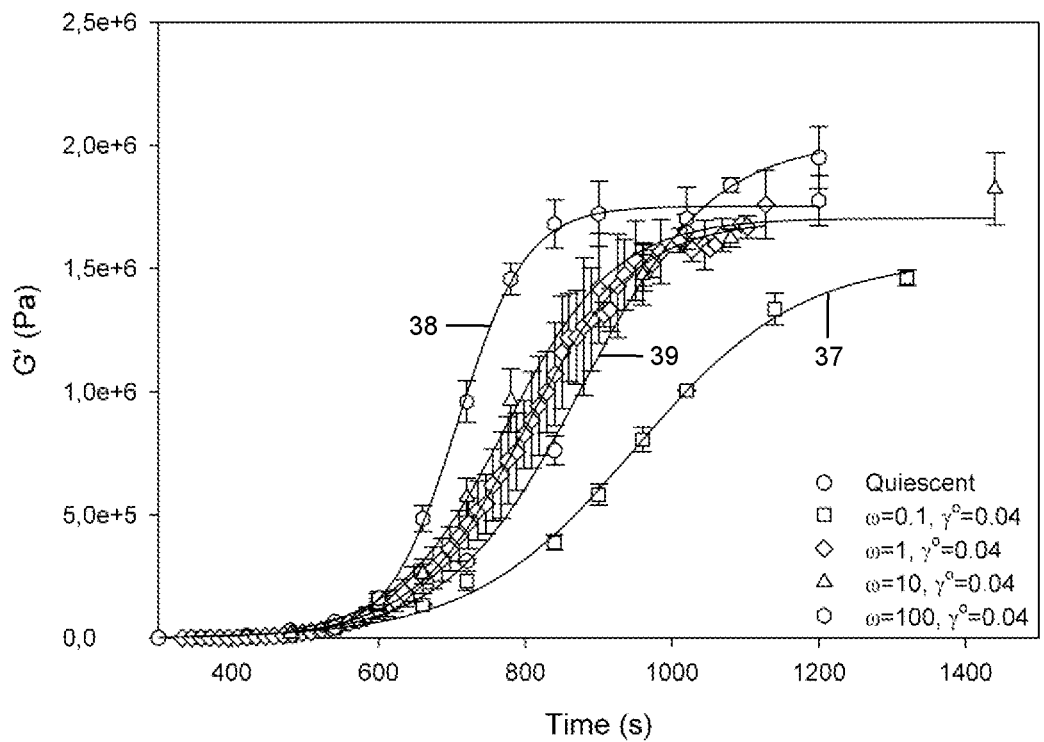
FIGS. 6A and 6B are a pair of charts showing the time-dependent development of the storage modulus (FIG.
Figure 6B:
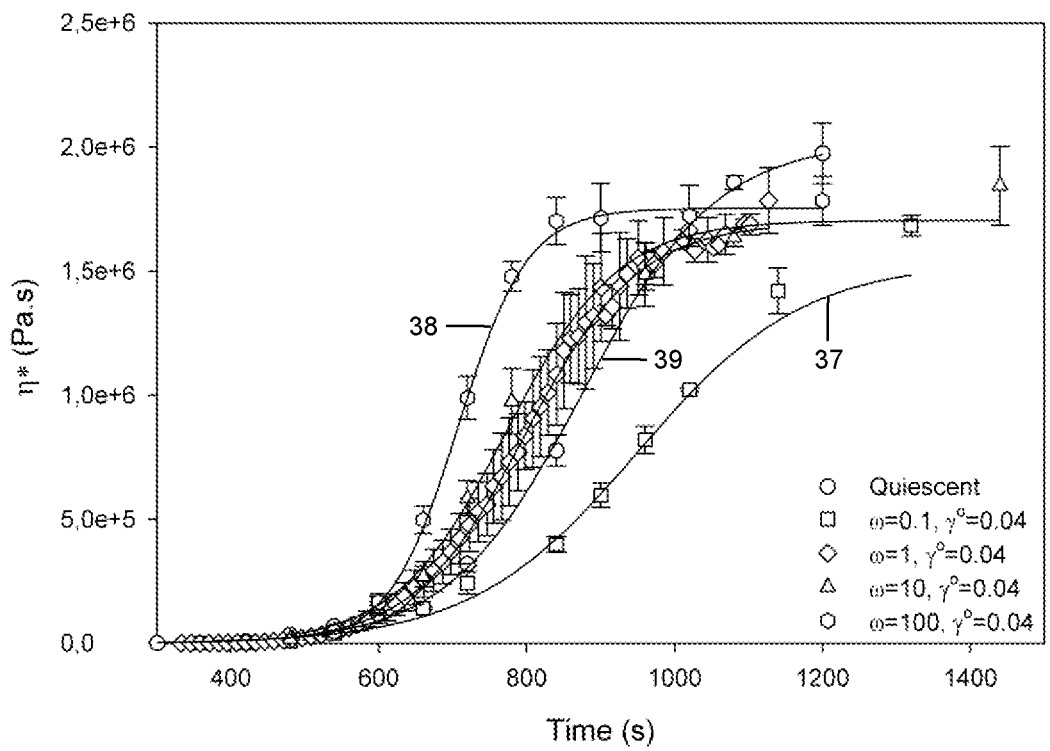

The comparisons of the time dependencies of the elasticity, i.e., the storage modulus, and the viscosity, i.e., the magnitude of complex viscosity, of brushite cement that were not presheared or were presheared at various frequencies at the same strain amplitude of 0.04 are presented in FIGS. 6A and 6B. It is worthwhile to emphasize again that these results are free from strain history and the associated shear thinning effects due to partitioning of the preshearing and measurement steps. Each data point was obtained from a statistically significant number of samples. These data are then curve fit into a sigmoidal function that is characteristic of cement setting in general. Delaying of the setting reaction 37 is observed for a low frequency of 0.1 rps. At this low strain amplitude the strains applied by oscillatory torsion are thought to affect the viscous liquid phase rather than the solid phase, slightly disrupting the crystal microstructure that develops with time. On the other hand, the setting rate of brushite cement increased gradually with increasing oscillation frequency at the same strain amplitude. Finally, at the frequency of 100 rps 38, the setting time decreased considerably in comparison to quiescent conditions 39. The increase in the setting rate with higher frequencies of oscillation is thought to result from enhanced dissolution and the consequent rise in the supersaturation of the crystallizing brushite phase by the agitation of the viscous liquid phase. This mechanism seems to dominate over the slight disruption of crystallization, reaching its maximum effect at the maximum frequency of 100 rps 38. At this preshearing condition the final setting time is shifted to about 800 seconds, indicating a decrease in setting time of about 400 seconds compared to cement sample that is kept under quiescent conditions 39. Therefore, the kinetics of the setting reaction can be altered in both directions via the adjustment of the frequency at the low strain amplitude of 0.04.

Thus, the typical results provided in FIGS. 6A and 6B indicate that cement formulations would be sensitive to preshearing at critical frequencies at a constant strain amplitude below the linear viscoelastic strain limit. Above a critical frequency the setting time would be shortened and below a critical frequency the setting time would be increased. The critical values of the frequencies can be determined a priori by carrying out such experiments in a rheometer device functioning simultaneously as a preshearing device and as a mechanical spectrometer. Thus, assuming that similar drag shear oscillation frequencies and strain amplitudes are generated in a preshearing device in a surgery setting the surgeon would have the options of increasing or decreasing the setting rate of the cement paste by selecting the appropriate preshearing conditions.

The effects of changes in the strain amplitude (this is representative of the angular displacement of the disk of the rheometer over the gap) used during preshearing on the time-dependent development of the elasticity and viscosity of the paste are shown in FIGS. 7A and 7B (at a constant frequency of 1 rps). In comparison to lower strain amplitudes a strain amplitude of 1, 40 caused significant delay in the setting of the cement paste. The initial and final setting times more than doubled with a slight increase in strain amplitude at a relatively low frequency of 1 rps. It is clear from these results that the parameters of oscillatory preshearing, i.e., frequency and strain amplitude both have significant roles in the time dependent development of elasticity and viscosity of cement pastes. The latter has a particularly strong effect on the development of elasticity as represented by the storage modulus above the linear viscoelastic strain limit for a specific oscillation frequency. The delaying of cement setting induced at this condition has a wide range of extents from a few seconds to hours depending on the frequency of the applied disruptive force on the intergrowing crystal structure that is driven by the dissolution and crystallization thermodynamics.

The comparisons of the time-dependent changes in the viscosity of the cement paste following preshearing that is based on oscillatory shear versus steady torsional flow are shown in FIGS. 8A and 8B. Both the viscosity and the elasticity (not shown) grow significantly slower with steady torsional flow 41, 42 in comparison to oscillatory shear. In oscillatory shear the strain is cyclic (sinusoidal) whereas in steady torsional flow the strain that is imposed is equal to the strain rate multiplied with the time. The application of steady torsional flow even at relatively low shear rates may eventually disrupt the network structure of the paste and increase the setting time significantly, giving rise to a significant increase in the injectability time window of the cement paste. Mild strain rates 42 typically retard cement setting such that the average yield strength of the cement structure is exceeded relatively earlier and multiple times. This retardation is caused by the continuous disruption of cement network structure the growth rate of which competes with the shear strain rate. Depending on the magnitude of steady shear strain rate, the disrupted cement microstructure may recover completely as the growing crystals are able to accommodate the applied strains or go through a series of recovery-disruption cycles that lead to a weakly set cement.

Example 2

The cement precursors in Example #1 without seed particles were mixed at a powder/liquid ratio of 1.0 and citric acid concentration of 0.1 M. Here the effects of preshearing are followed via systematic changes in the frequency as well as the strain amplitude. FIGS. 10A and 10B show that as the frequency of the preshearing is Increased at a constant strain magnitude of 1, the setting of the cement paste is delayed significantly with increasing frequency, consistent with the findings associated with Example #1. Despite the fact that applied strain amplitude of 1 was greater the linear viscoelastic strain limit for this cement formulation, preshearing at a frequency of 0.1 rps and strain amplitude of 1, 43 resulted in setting kinetics similar to the quiescently set cement (not shown). Further increasing the frequency at this relatively high strain amplitude to 1 rps, 44 and 10 rps, 45 slowed down the setting proportionally.

FIG. 10 shows the effect of the strain amplitude on the storage modulus, G', of the same cement formulation at the same oscillation frequency of 1 rps. The strain amplitude of 0.1 is lower than the linear viscoelastic strain limit for this formulation and results in similar setting kinetics 46 with the quiescently set cement (not shown). On the other hand a high strain amplitude of 100 applied at the same frequency 47 significantly delayed the development of the crystal network. Clearly the strain amplitude provides another controlling variable with Increasing strain amplitude delaying further the setting reaction and increasing the injectability/extrudability of the cement paste.

Example 3

The application of interrupted cyclic deformation of the ceramic paste (cyclic increase and then decrease of the frequency) versus continuously oscillated (at constant frequency and strain amplitude) was tested using the cement precursors of Example #1 with a powder/liquid ratio of 0.8 and citric acid concentration of 0.4. The effects of stepwise cyclic change in applied frequency on bone cement dynamic rheological properties were investigated by varying the frequency from 0.1 rps to 1 rps, from 0.1 rps to 10 rps, or from 0.1 to 100 rps as well as increasing the number of times the frequency is altered during the course of total deformation period. The frequency was altered between 4 and 15 number of times. The schemes for cyclic changes in frequency between 0.1 rps to 100 rps in conjunction with three different number of cycles over the total deformation period are shown in FIG. 11A, FIG. 11B, and FIG. 11C. The application times for each step change 48, 49, 50 varied from 250 to 170 to 100 seconds respectively with a concomitant increase in the number of cycles applied for a given total duration.

FIG. 12 shows the storage modulus, G', (indicative of the elasticity of the paste) upon the application of five different preshearing modes. In two of the runs the frequency has been kept constant at 0.1 rps, 51 and 100 rps, 52 during preshearing. On the other hand, the frequency has been cyclically shifted between 0.1 and 100 rps with different periods over the course of the total duration of the experiment under the other three preshearing conditions. When the period of the application is rather long, for example, when each frequency is applied for a duration of 250 s (this is indicated as 4 shearing cycles) the cyclic alteration of frequency 53 does not lead to any retardation in the setting time over the application of a constant frequency during the deformation. On the contrary, the setting kinetics was promoted (decrease of the setting time) at a small number of 4 cycles possibly due to agitation of the liquid phase during frequency shifts. However, when the period of the application of each frequency is reduced to 100 s (this is indicated as 14 shearing cycles), i.e., the frequency is shifted from 0.1 to 100 rps repetitively for 100 s durations at each frequency, the dynamic properties of the paste 54 decrease considerably in comparison to samples subjected to oscillatory shear at constant frequencies of 0.1 and 100 rps. Thus, these results suggest that various other cyclic modes than continuous shearing or continuous oscillation can even be more effective in prolonging setting time and increasing the injectable time window of the cementitious ceramic pastes.

All examples and conditional language recited herein are intended for pedagogical purposes to aid the reader in understanding the principles of the invention and the concepts contributed by the inventor to furthering the art, and are to be construed as being without limitation to such specifically recited examples and conditions. Moreover, all statements herein reciting principles, aspects, and embodiments of the invention, as well as specific examples thereof, are intended to encompass both structural and functional equivalents thereof. Additionally, It is intended that such equivalents Include both currently known equivalents as well as equivalents developed in the future, i.e., any elements developed that perform the same function, regardless of structure.

It will be understood that the embodiments described herein are merely exemplary and that a person skilled in the art may make many variations and modifications without departing from the spirit and scope of the invention. Certain features that are described in this specification in the context of separate embodiments can also be implemented in combination in a single embodiment. Conversely, various features that are described in the context of a single embodiment can also be implemented in combination in multiple embodiments separately or in any suitable sub-combination. Moreover, although features may be described above as acting in certain combinations and even initially claimed as such, one or more features from a claimed combination can in some cases be excised from the combination, and the claimed combination may be directed to a sub-combination or variation of a sub-combination. All such variations and modifications are Intended to be included within the scope of the invention.

We claim:

1. A method of controlling aqueous inorganic cements in surgical procedures, the method comprising:
   characterizing setting kinetics by monitoring variations of dynamic rheological properties of aqueous inorganic cement with respect to time, temperature, and shearing conditions after quiescent periods in a rotational rheometer; the rotational rheometer having an ability to generate steady and oscillatory torsion;
   pinpointing a characteristic linear viscoelastic strain or stress limit, dough time, initial setting time, and final setting time;
   subjecting a cement paste to preshearing periods of various oscillatory preshearing frequencies at a strain or stress amplitude lower than a predetermined linear viscoelastic strain or stress limit;
   measuring the dynamic rheological properties at an end of the preshearing periods;
   comparing the dynamic rheological properties of the cement paste at the end of the preshearing periods to the dynamic rheological properties of the quiescently tested cements;
   pinpointing a characteristic setting promoting frequency limit;
   applying a time dependent preshearing period to the cement paste with the facility of a drag flow mechanism comprising a screw in contact with the cement paste, that can independently rotate in both a clockwise direction and a counterclockwise direction and can alternate between rotation in the clockwise direction and the counterclockwise direction in a cyclic manner, to promote or delay setting of the cement paste by adjusting oscillatory strain amplitude and frequency;
   delivering the cement paste to a surgical site after application of the time dependent preshearing period.

2. The method of claim 1, wherein the dynamic rheological properties are a magnitude of complex viscosity, a storage modulus, and a loss modulus.

3. The method of claim 1, wherein the presheared cement paste can be delivered with an extrusion mechanism through steady torsion of a screw element or with a syringe mechanism through displacement of a plunger element.

4. The method of claim 1, wherein the presheared cement paste is utilized in the surgical procedures including spinal fusion, vertebroplasty, khyphoplasty, cranioplasty, periodontal and endodontal surgeries, or tissue engineering scaffold manufacturing through robotic delivery.

5. The method of claim 1, wherein the aqueous inorganic cements are ceramic phases of sodium silicate, calcium oxide, calcium hydroxide, calcium aluminate, calcium sulphate, calcium silicate, calcium aluminum silicate, calcium sulphoaluminate, zinc phosphate, zinc oxychloride, magnesium oxide, magnesium hydroxide, magnesium phosphate, magnesium oxychloride, magnesium oxysulphate, calcium carbonate or calcium phosphate.

6. The method of claim 1, wherein a binder liquid phase of an inorganic cementitious suspension is pure water or an aqueous solution of water and water soluble chemicals including, sodium chloride, sodium tetraborate, citric acid, orthophosphoric acid, silicic acid, sulphuric acid, polyacrylic acid and the alkali salts of these acids.

* * * * *